US012789118B2

(12) United States Patent
De Santi Ungarato et al.

(10) Patent No.: US 12,789,118 B2
(45) Date of Patent: Nov. 10, 2026

(54) FOAM CONTROL AGENT

(71) Applicant: Dow Global Technologies LLC, Midland, MI (US)

(72) Inventors: Rafael F. De Santi Ungarato, Jundiaí (BR); Xue Chen, Manvel, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 660 days.

(21) Appl. No.: 18/248,531

(22) PCT Filed: Oct. 21, 2021

(86) PCT No.: PCT/US2021/055933
§ 371 (c)(1),
(2) Date: Apr. 11, 2023

(87) PCT Pub. No.: WO2022/093606
PCT Pub. Date: May 5, 2022

(65) Prior Publication Data

US 2024/0001262 A1 Jan. 4, 2024

Related U.S. Application Data

(60) Provisional application No. 63/105,375, filed on Oct. 26, 2020.

(51) Int. Cl.

| | |
|---|---|
| ***B01D 19/04*** | (2006.01) |
| ***C07C 31/125*** | (2006.01) |
| ***C12P 7/06*** | (2006.01) |

(52) U.S. Cl.
CPC ........ *B01D 19/0404* (2013.01); *C07C 31/125* (2013.01); *C12P 7/06* (2013.01)

(58) Field of Classification Search
CPC ..... B01D 19/0404; C07C 31/125; C12P 7/06; Y02E 50/10; C11D 3/0026; C11D 3/2017; C11D 3/202
See application file for complete search history.

(56) References Cited

U.S. PATENT DOCUMENTS

| | | | | |
|---|---|---|---|---|
| 8,357,823 | B2 * | 1/2013 | Wurm ................ | C08G 65/2609 568/679 |
| 9,018,266 | B2 | 4/2015 | Matani et al. | |
| 9,150,886 | B2 | 10/2015 | Oliveira et al. | |
| 2010/0075389 | A1 | 3/2010 | Wurm et al. | |
| 2018/0002635 | A1 | 1/2018 | Shearouse et al. | |

FOREIGN PATENT DOCUMENTS

| | | | | |
|---|---|---|---|---|
| WO | WO-2019177726 A1 * | 9/2019 | ............. | A23L 29/00 |

OTHER PUBLICATIONS

Junker, "Foam and Its Mitigation in Fermentation Systems", Biotechno. Prog., 2007, vol. 23, pp. 767-784.
PCT/US2021/055933 International Search Report and Written Opinion with a mailing date of Feb. 14, 2022.

* cited by examiner

*Primary Examiner* — Deborah D Carr

(57) ABSTRACT

A foam control agent and method of controlling foam for bioethanol processing by use of a foam control agent, wherein the agent comprises at least a branched alcohol.

4 Claims, No Drawings

FOAM CONTROL AGENT

Embodiments relate to a foam control agent and method of controlling foam for bioethanol processing, wherein the agent comprises at least a branched alcohol.

INTRODUCTION

Ethanol may be produced through a biological fermentation process from sugarcane feedstocks. Such ethanol is termed bioethanol (sometimes noted as bio-ethanol) and the process to produce this ethanol is frequently bogged down by the presence of foam created by yeasts in the production media. The yeasts are added to a fermentation tank with a continuous supply of the sugarcane feedstocks to produce bioethanol. Uncontrolled foaming in these tanks can result in a significant loss in production capacity. The foaming can cause overflows which result in spills and product waste. Foaming during ethanol production is a major challenge and thus mechanical methods of foam management have been devised with limited effectiveness.

Foam control agents (FCA) are widely considered more practical than the mechanical methods and are currently more commonly employed across the industry to minimize production losses due to foaming. These foam control agents can include both defoaming and anti-foaming chemicals. Antifoamers (a term of art) are designed to prevent foam, whereas defoamers (another term of art) eliminate existing foam.

For fermentation applications, foam control agents typically include block copolymers (polyglycols) composed of ethylene oxide, propylene oxide, and/or butylene oxide. These types of products are effective since, it is believed that at increased temperatures, they are insoluble in solution, thereby causing an increase in the surface tension of the system, which results in foam collapse. Generally, these materials are combined with other hydrophobic materials to improve the foam control properties. The use of these foam control agents is critical to the industry and thus any novel or improved foam control agent is highly useful.

For all these reasons and more, there is a need for a foam control agent and method of controlling foam for bioethanol processing.

SUMMARY

Embodiments relate to a foam control agent and method of controlling foam for bioethanol processing, wherein the agent comprises at least a branched alcohol.

DETAILED DESCRIPTION

The present disclosure relates to a foam control agent for bioethanol production. As previously discussed, ethylene oxide, propylene oxide, and/or butylene oxide are commonly used foam control agents. The present disclosure details how, unexpectedly, branched alcohols have been shown to have superior foam control performance. This performance is better at foam control than even alkoxylated copolymers (polyglycols, both diols and triols as initiator), which enables these materials to be utilized as foam control agents in bioethanol fermentation applications. The branched alcohols may be 2-alkyl-1-alkanols (also known as Guerbet alcohols), and preferably 2-ethylhexanol (2-EH) and 2-propylheptanol (2-PH). These alcohols can be synthesized via the aldol condensation of the corresponding aldehydes or from the Guerbet reaction of primary linear alcohols. Other methods of production may also be utilized.

The generic structure of the antifoaming agent currently disclosed is as follows:

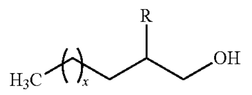

wherein x is an integer from 2 to 14 and R is an alkyl group with 1-14 carbon atoms.

The foam control agent may also be described as comprising a 2-alkyl substituted alcohol from C8-C32. The alcohols can be predominately one isomer (>95 wt. %) or a mixture of alcohols which can be generated by an aldol condensation of a mixture of aldehydes or generated from a mixture of alcohols via the Guerbet reaction.

The C8-C32 Guerbet alcohols including 2-ethylhexanol and 2-propylheptanol and the mixture of C8, C9, and C10 alcohols generated from the aldol condensation of butyraldehyde and valeraldehyde are preferred in some embodiments.

The concentration of the Guerbet alcohol in the formulated foam control agent ranges from 0.01% to 100%, preferably, ranging from 40% to 100% when used as antifoaming agent and ranging from 0.01% to 25% when used as defoaming agent. The Guerbet alcohol can be in the form of a solid or liquid, a liquid is preferred. If it is a solid, the material may be dissolved or dispersed in a solvent. The said foam control agent can be aqueous solution or organic solvent based solution. The usage dosage of the said foam control agent for bioethanol fermentation processing ranges from 10 to 10000 ppm in relation to the total amount of liquids present in the fermentation tank. Preferably, ranges from 50 to 1000 ppm, when the same is used as antifoaming agent. When used as defoaming agent, its dosage ranges from 10 to 500000 ppm, preferably from 50 to 10000 ppm.

Other foam control agents (e.g., copolymers composed of ethylene oxide, propylene oxide, and/or butylene oxide, random or blocks) or other hydrophobic materials such as waxes, oils or silicas may also be added with the branched, Guerbet alcohol(s). Silicone can be used in conjunction with the 2-alkyl alcohols. Surfactants, especially alkoxylates of the alcohols can also be used. The use of branched alcohols as foam control agents may be water based or oil based.

The new foam control agent presently disclosed may be in the form of a solid or liquid. If it is a solid, the material may be dissolved or dispersed in a solvent before use as a foam control agent. The presently disclosed agents are believed to work in the presence of all commonly used bioethanol fermentation yeasts that can generate foam including, but not limited to, different strains of: *Saccharomyces Cerevisiae, Candida Albicans, Schizosaccharomyces, Brettanomyces* and others.

The chemical agent can be used both in antifoamer or defoamer formulations. Antifoamer formulations are obtained by the mixture of polyglycols, esters, silicones, solvents, water and other chemicals that in the gas-liquid interface of the bubble avoiding the foam formation. Other amphiphilic chemicals based on block copolymer can be used as well. In defoaming formulations, in addition to the products mentioned above, it can be used vegetal oils, mineral oils, waxes and other oily agents.

The currently disclosed foam control agent can be used as a booster or the main component of such formulations and it can be used to prevent or breakdown the foam. In sugarcane mills this means that the product can be used in yeast treatment tanks or in fermentation tank themselves. It can also be used for sugar beet and potato processing to minimize foam. The agent can be used continuously or batched, being highly suitable for any type of mill operation.

This chemical can be added in the tank, where the yeast is treated with acid and other chemicals; or be added in the fermentation tank before, during, or after the addition of the sugar solution. Fermentation is usually conducted at temperatures lower than 34° C. This temperature is obtained by the use of heat exchangers. After the dispersion of yeast has been transferred to the fermentation tank, the feed of the sugar solution can take a good deal of time (up to 6 or 8 hours) and during this time period is where the greatest foaming occurs. After the sugar solution feeding, some additional time can be required to ensure an effective conversion of sugar in ethanol. This additional period can vary from 1-4 hours for to a total time of 12 hours from the beginning of the feeding of the sugar solution. The current product is indicated to be used during the entire duration of the fermentation process.

The foam control agent, as mentioned above, may optionally further include a solvent, a surfactant, an emulsifier, or a combination thereof. The foam control agent in one embodiment contains from 0.01 to 100 percent, by weight, of the composition of branched alcohol. Alternatively, the foam control agent may contain from 5 to 100 percent, by weight, of the composition of the branched alcohol; 10 to 100 percent, by weight, of the composition of the branched alcohol; 15 to 100 percent, by weight, of the composition of the branched alcohol; 20 to 100 percent, by weight, of the composition of the branched alcohol; 25 to 100 percent, by weight, of the composition of the branched alcohol; or even 30 to 100 percent, by weight, of the composition of the branched alcohol.

The optional solvent contained in the foam control agent is selected to be suitable for dissolving or dispersing the composition the branched alcohol. Such solvents may include water, hydrocarbons (both aromatic and aliphatic), and oxygenated solvents (alcohols, ketones, aldehydes, ethers, glycol ethers, esters, and glycol ether esters).

The optional surfactant or emulsifier contained in the foam control agent is selected to be suitable for improving the compatibility of the foam control agent on the feedstock or forming an emulsion with the composition of branched alcohol. The optional surfactant or emulsifier has an amount ranging from 0.1-30% by weight of the composition of branched alcohol.

The optional surfactant or emulsifier may be anionic, cationic or nonioic. Examples of suitable anionic surfactants or emulsifiers are alkali metal, ammonium and amine soaps; the fatty acid part of such soaps contains preferably at least 10 carbon atoms. The soaps can also be formed "in situ;" in other words, a fatty acid can be added to the oil phase and an alkaline material to the aqueous phase.

Other examples of suitable anionic surfactants or emulsifiers are alkali metal salts of alkyl-aryl sulfonic acids, sodium dialkyl sulfosuccinate, sulfated or sulfonated oils, e.g., sulfated castor oil; sulfonated tallow, and alkali salts of short chain petroleum sulfonic acids.

Suitable cationic surfactants or emulsifiers are salts of long chain primary, secondary or tertiary amines, such as oleylamide acetate, cetylamine acetate, di-dodecylamine lactate, the acetate of aminoethyl-aminoethyl stearamide, dilauroyl triethylene tetramine diacetate, 1-aminoethyl-2-heptadecenyl imidazoline acetate; and quaternary salts, such as cetylpyridinium bromide, hexadecyl ethyl morpholinium chloride, and diethyl di-dodecyl ammonium chloride.

Examples of suitable nonionic surfactants or emulsifiers are condensation products of higher fatty alcohols with ethylene oxide, such as the reaction product of oleyl alcohol with 10 ethylene oxide units; condensation products of alkylphenols with ethylene oxide, such as the reaction product of isoctylphenol with 12 ethylene oxide units; condensation products of higher fatty acid amides with 5, or more, ethylene oxide units; polyethylene glycol esters of long chain fatty acids, such as tetraethylene glycol monopalmitate, hexaethyleneglycol monolaurate, nonaethyleneglycol monostearate, nonaethyleneglycol dioleate, tridecaethyleneglycol monoarachidate, tricosaethyleneglycol monobehenate, tricosaethyleneglycol dibehenate, polyhydric alcohol partial higher fatty acid esters such as sorbitan tristearate, ethylene oxide condensation products of polyhydric alcohol partial higher fatty acid esters, and their inner anhydrides (mannitol-anhydride, called Mannitan, and sorbitol-anhydride, called Sorbitan), such as glycerol monopalmitate reacted with 10 molecules of ethylene oxide, pentaerythritol monooleate reacted with 12 molecules of ethylene oxide, sorbitan monostearate reacted with 10-15 molecules of ethylene oxide, mannitan monopalmitate reacted with 10-15 molecules of ethylene oxide; long chain polyglycols in which one hydroxyl group is esterified with a higher fatty acid and other hydroxyl group is etherified with a low molecular alcohol, such as methoxypolyethylene glycol 550 monostearate (550 meaning the average molecular weight of the polyglycol ether). A combination of two or more of these surfactants may be used; e.g., a cationic may be blended with a nonionic or an anionic with a nonionic.

The foam control agent may further comprise one or more additives. Examples of additives include ethylene oxide/propylene oxide block copolymers, butylene oxide/propylene oxide block copolymers, ethylene oxide/butylene oxide block copolymers, waxes, or silicone-based materials.

EXAMPLES

An experiment to test the efficacy of the presently disclosed foam control agent and others may be conducted using Fermentest equipment as follows.

The chemicals used as foam control agents are commercially available from The Dow chemical Company under the trademarks of FLUENT-CANE™ 149 and FLUENT-CANE™ 178. 2-ethylhexanol (2-EH) and 2-propylheptanol (2-PH) were commercially available from Sigma Aldrich.

The different strain yeast used were obtained from LNF, a local company in Brazil. For all experiments, a 20 wt % sugar solution is created with tap water, in order to obtain 20 Degrees Brix (° Bx) along with 10 wt % yeast (all different strains of *Saccharomyces Cerevisiae*, also diluted in tap water). The specific different strains of the same yeast (*Saccharomyces cerevisiae*) used for this study were CAT, PE2, Fermel and Fleischman. All the yeasts were obtained in a dry form and it was necessary to hydrate them. A blank, without the addition of any foam control chemicals, was also run as a control in order to have a better comparison for analysis. Table 1 provides a listing of which strain and foam control agent to be used for each example.

TABLE 1

| Name | Strain | Foam control agent |
|---|---|---|
| Example 1 | CAT | 2-EH |
| Example 2 | PE2 | 2-EH |
| Example 3 | Fermel | 2-EH |
| Example 4 | Fleischman | 2-EH |
| Example 5 | CAT | 2-PH |
| Example 6 | PE2 | 2-PH |
| Example 7 | Fermel | 2-PH |
| Example 8 | Fleischman | 2-PH |
| Comparative Example 1 | CAT | blank |
| Comparative Example 2 | PE2 | blank |
| Comparative Example 3 | Fermel | blank |
| Comparative Example 4 | Fleischman | blank |
| Comparative Example 5 | CAT | FLUENT-CANE ™ 149 |
| Comparative Example 6 | PE2 | FLUENT-CANE ™ 149 |
| Comparative Example 7 | Fermel | FLUENT-CANE ™ 149 |
| Comparative Example 8 | Fleischman | FLUENT-CANE ™ 149 |
| Comparative Example 9 | CAT | FLUENT-CANE ™ 178 |
| Comparative Example 10 | PE2 | FLUENT-CANE ™ 178 |
| Comparative Example 11 | Fermel | FLUENT-CANE ™ 178 |
| Comparative Example 12 | Fleischman | FLUENT-CANE ™ 178 |

A certain amount (e.g., 0.135 g) of the foam control agent is added into the mixture of 300 g of the yeast preparation and 600 g of the sugar solution. In this example, the addition of 0.135 g of foam control agent amounts to around 150 ppm foam control agent in relation to total weight of 900 g of the solutions added into Fermentest equipment. The total mass was then transferred to a cylindrical vessel, in which air was injected via a porous plate.

After this, a 7.0 L/min airflow rate was passed through the porous plate (16-40 mm pore size) and the time required for the foam to reach 25 cm height was measured. This demonstrated the differences in foam behavior and in the ability of each tested agent to retain the foam height in comparison with each yeast strain. The longer the time to reach the foam height, the better the product performance. This parameter is represented as Time to 25 cm (T25) in Table 2.

TABLE 2

| Name | Strain | Foam control agent | Time to reach 25 cm height (second) |
|---|---|---|---|
| Example 1 | CAT | 2-EH | 71.3 ± 7.1 |
| Example 2 | PE2 | 2-EH | 47.4 ± 7.2 |
| Example 3 | Fermel | 2-EH | 57.3 ± 13.3 |
| Example 4 | Fleischman | 2-EH | 134.7 ± 10.5 |
| Example 6 | CAT | 2-PH | 57.7 ± 2.2 |
| Example 7 | PE2 | 2-PH | 47.3 ± 2.7 |
| Example 8 | Fermel | 2-PH | 45.0 ± 1.2 |
| Example 9 | Fleischman | 2-PH | 161.8 ± 10.5 |
| Comparative Example 1 | CAT | blank | 49.2 ± 8.5 |
| Comparative Example 2 | PE2 | blank | 35.6 ± 4.0 |
| Comparative Example 3 | Fermel | blank | 33.4 ± 2.5 |
| Comparative Example 4 | Fleischman | blank | 49.3 ± 5.0 |
| Comparative Example 6 | CAT | FLUENT-CANE ™ 149 | 83.7 ± 18.9 |
| Comparative Example 7 | PE2 | FLUENT-CANE ™ 149 | 46.2 ± 2.9 |
| Comparative Example 8 | Fermel | FLUENT-CANE ™ 149 | 40.0 ± 0.6 |
| Comparative Example 9 | Fleischman | FLUENT-CANE ™ 149 | 65.3 ± 6.3 |
| Comparative Example 11 | CAT | FLUENT-CANE ™ 178 | 87.3 ± 3.1 |
| Comparative Example 12 | PE2 | FLUENT-CANE ™ 178 | 55.9 ± 9.0 |
| Comparative Example 13 | Fermel | FLUENT-CANE ™ 178 | 44.2 ± 2.9 |
| Comparative Example 14 | Fleischman | FLUENT-CANE ™ 178 | 53.6 ± 2.2 |

Comparing all the yeast strains with all the foam control agents, we surprisingly found a higher value for time to reach 25 cm was obtained when 2-Propylheptanol and 2-ethyl hexanol were used to control the foam generated by Fleishman strain. This strain is one of the main used by sugarcane mills, since its price is much lower than the others. Thus, the use of such foam control agents for bioethanol production would be highly desirable.

The invention claimed is:

1. A method of controlling foam for bioethanol processing by use of a foam control agent, wherein the agent comprises at least one of 2-ethylhexanol and 2-propylheptanol and wherein the bioethanol fermentation comprises the Fleischmann strain of yeast.

2. The method of claim 1, wherein at least one other foam control agent or hydrophobic material is added.

3. The method of claim 1, wherein silicone or a surfactant is also added when processing bioethanol.

4. The method of claim 1, wherein the bioethanol processing is conducted in a fermentation tank and the branched alcohol concentration is from 1 to 500000 ppm in the fermentation tank.

* * * * *